(12) United States Patent
Johnson et al.

(10) Patent No.: US 8,948,858 B2
(45) Date of Patent: Feb. 3, 2015

(54) METHOD AND APPARATUS FOR IDENTIFYING POTENTIALLY MISCLASSIFIED ARRHYTHMIC EPISODES

(75) Inventors: Christopher Dale Johnson, Playa Del Ray, CA (US); Alok Sathaye, Boston, MA (US); Shelley Cazares, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 549 days.

(21) Appl. No.: 12/769,851

(22) Filed: Apr. 29, 2010

(65) Prior Publication Data

US 2010/0211125 A1   Aug. 19, 2010

Related U.S. Application Data

(63) Continuation of application No. 11/643,221, filed on Dec. 21, 2006, now Pat. No. 7,738,950.

(60) Provisional application No. 60/844,253, filed on Sep. 13, 2006.

(51) Int. Cl.
*A61B 5/04* (2006.01)
*A61B 5/00* (2006.01)
(Continued)

(52) U.S. Cl.
CPC ............ *A61B 5/7264* (2013.01); *A61B 5/02405* (2013.01); *A61B 5/0245* (2013.01);
(Continued)

(58) Field of Classification Search
CPC ........ A61B 5/02; A61B 5/0205; A61B 5/024; A61B 5/0245; A61B 5/04; A61B 5/0402; A61B 5/0432; A61B 5/0452; A61B 5/0464

USPC ............ 600/508–528; 607/1–5, 7–18, 25, 62, 607/115, 119, 122, 123; 128/897–899
See application file for complete search history.

(56) References Cited

U.S. PATENT DOCUMENTS 4,023,564 A   5/1977   Valiquette et al.
4,336,810 A   6/1982   Anderson et al.
(Continued)

FOREIGN PATENT DOCUMENTS

EP   0360412   3/1990
EP   0450943   4/1991
(Continued)

OTHER PUBLICATIONS

Dubin, "Rapid Interpretation of EKG's", 2000, Cover Publishing Company, 6th edition, p. 3334-345.
(Continued)

*Primary Examiner* — Christopher D Koharski
*Assistant Examiner* — Elizabeth K So
(74) *Attorney, Agent, or Firm* — Schwegman Lundberg & Woessner, P.A.

(57) ABSTRACT

An implantable cardiac device is configured to classify cardiac arrhythmias using a plurality of arrhythmia discrimination algorithms. Data is provided that is associated with a plurality of cardiac arrhythmic episodes for which a cardiac electrical therapy was delivered or withheld by the implantable medical device based on the plurality of arrhythmia discrimination algorithms. A metric for each of the arrhythmic episodes is computed. The metric defines a measure by which the implantable cardiac device properly classified the arrhythmia. Potentially misclassified arrhythmic episodes of the plurality of cardiac arrhythmic episodes for which cardiac electrical therapy was inappropriately delivered or withheld are algorithmically identified using the metric.

20 Claims, 9 Drawing Sheets

(51) Int. Cl.
  *A61B 5/024* (2006.01)
  *A61B 5/0245* (2006.01)
  *A61B 5/0452* (2006.01)
  *A61B 5/0464* (2006.01)
  *G06F 19/00* (2011.01)
  *A61N 1/372* (2006.01)

(52) U.S. Cl.
  CPC ........... *A61B5/04525* (2013.01); *A61B 5/0464* (2013.01); *A61B 5/6846* (2013.01); *G06F 19/3481* (2013.01); *A61B 5/04* (2013.01); *A61B 5/726* (2013.01); *A61N 1/37247* (2013.01)
  USPC ........................................................ 600/515

(56) References Cited

U.S. PATENT DOCUMENTS

| | | |
|---|---|---|
| 4,428,378 A | 1/1984 | Anderson et al. |
| 4,550,221 A | 10/1985 | Mabusth |
| 4,686,332 A | 8/1987 | Greanias et al. |
| 4,865,036 A | 9/1989 | Chirife |
| 4,872,459 A | 10/1989 | Pless et al. |
| 4,880,005 A | 11/1989 | Pless et al. |
| 5,144,947 A | 9/1992 | Wilson |
| 5,161,527 A | 11/1992 | Nappholz et al. |
| 5,176,137 A | 1/1993 | Erickson |
| 5,217,021 A | 6/1993 | Steinhaus et al. |
| 5,257,621 A | 11/1993 | Bardy et al. |
| 5,312,445 A | 5/1994 | Nappholz et al. |
| 5,330,505 A | 7/1994 | Cohen |
| 5,330,508 A | 7/1994 | Gunderson |
| 5,411,031 A | 5/1995 | Yomtov |
| 5,447,519 A | 9/1995 | Peterson |
| 5,458,620 A | 10/1995 | Adams et al. |
| 5,554,177 A | 9/1996 | Kieval |
| 5,725,559 A | 3/1998 | Alt et al. |
| 5,779,645 A | 7/1998 | Olson et al. |
| 5,782,819 A | 7/1998 | Tanzer et al. |
| 5,782,888 A | 7/1998 | Sun et al. |
| 5,817,027 A | 10/1998 | Arand et al. |
| 5,844,506 A | 12/1998 | Binstead |
| 5,846,263 A | 12/1998 | Peterson et al. |
| 5,857,977 A | 1/1999 | Caswell et al. |
| 5,978,707 A | 11/1999 | Krig et al. |
| 6,076,014 A | 6/2000 | Alt |
| 6,147,680 A | 11/2000 | Tareev |
| 6,178,350 B1 | 1/2001 | Olson et al. |
| 6,192,273 B1 | 2/2001 | Igel et al. |
| 6,221,011 B1 | 4/2001 | Bardy |
| 6,223,078 B1 | 4/2001 | Marcovecchio |
| 6,230,055 B1 | 5/2001 | Sun et al. |
| 6,253,102 B1 | 6/2001 | Hsu et al. |
| 6,266,554 B1 | 7/2001 | Hsu et al. |
| 6,270,457 B1 | 8/2001 | Bardy |
| 6,275,732 B1 | 8/2001 | Hsu et al. |
| 6,275,734 B1 * | 8/2001 | McClure et al. ................ 607/27 |
| 6,277,072 B1 | 8/2001 | Bardy |
| 6,280,380 B1 | 8/2001 | Bardy |
| 6,308,095 B1 | 10/2001 | Hsu et al. |
| 6,312,378 B1 | 11/2001 | Bardy |
| 6,336,903 B1 | 1/2002 | Bardy |
| 6,358,203 B2 | 3/2002 | Bardy |
| 6,366,812 B1 * | 4/2002 | Levine et al. ................... 607/27 |
| 6,368,284 B1 | 4/2002 | Bardy |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,986 B1 | 6/2002 | Sun et al. |
| 6,418,340 B1 | 7/2002 | Conley et al. |
| 6,434,417 B1 | 8/2002 | Lovett |
| 6,438,407 B1 | 8/2002 | Ousdigian et al. |
| 6,438,410 B2 | 8/2002 | Hsu et al. |
| 6,440,066 B1 | 8/2002 | Bardy |
| 6,445,949 B1 | 9/2002 | Kroll |
| 6,449,503 B1 | 9/2002 | Hsu |
| 6,480,734 B1 | 11/2002 | Zhang et al. |
| 6,487,443 B2 | 11/2002 | Olson et al. |
| 6,564,106 B2 | 5/2003 | Guck et al. |
| 6,567,691 B1 * | 5/2003 | Stadler .......................... 600/515 |
| 6,594,523 B1 | 7/2003 | Levine |
| 6,611,713 B2 | 8/2003 | Schauerte |
| 6,631,290 B1 | 10/2003 | Guck et al. |
| 6,654,639 B1 | 11/2003 | Lu |
| 6,684,100 B1 | 1/2004 | Sweeney et al. |
| 6,708,058 B2 | 3/2004 | Kim et al. |
| 6,766,194 B1 | 7/2004 | Kroll |
| 6,801,806 B2 | 10/2004 | Sun et al. |
| 6,843,801 B2 | 1/2005 | Conley et al. |
| 6,882,883 B2 | 4/2005 | Condie et al. |
| 6,888,538 B2 | 5/2005 | Ely et al. |
| 6,889,079 B2 | 5/2005 | Bocek et al. |
| 6,909,916 B2 | 6/2005 | Spinelli |
| 6,922,585 B2 | 7/2005 | Zhou |
| 6,993,385 B1 | 1/2006 | Routh |
| 7,031,764 B2 | 4/2006 | Schwartz et al. |
| 7,076,289 B2 | 7/2006 | Sarkar et al. |
| 7,085,599 B2 | 8/2006 | Kim et al. |
| 6,084,253 A1 | 9/2006 | Johnson et al. |
| 7,103,405 B2 | 9/2006 | Sakar et al. |
| 7,107,098 B2 | 9/2006 | Sharma et al. |
| 7,129,935 B2 | 10/2006 | Mackey |
| 7,130,677 B2 | 10/2006 | Brown et al. |
| 7,130,678 B2 | 10/2006 | Ritscher et al. |
| 7,184,815 B2 | 2/2007 | Kim et al. |
| 7,228,173 B2 | 6/2007 | Cazares |
| 7,228,176 B2 * | 6/2007 | Smith et al. ..................... 607/28 |
| 7,277,747 B2 | 10/2007 | Cazares et al. |
| 7,653,431 B2 | 1/2010 | Cazares et al. |
| 7,738,950 B2 | 6/2010 | Johnson et al. |
| 2002/0183637 A1 | 12/2002 | Kim et al. |
| 2003/0191403 A1 | 10/2003 | Zhou et al. |
| 2004/0093035 A1 | 5/2004 | Schwartz et al. |
| 2004/0111119 A1 | 6/2004 | Sarkar et al. |
| 2004/0111120 A1 | 6/2004 | Sarkar et al. |
| 2004/0111121 A1 | 6/2004 | Brown et al. |
| 2004/0167579 A1 | 8/2004 | Sharma et al. |
| 2004/0176694 A1 | 9/2004 | Kim et al. |
| 2004/0215092 A1 | 10/2004 | Fischell et al. |
| 2005/0038478 A1 * | 2/2005 | Klepfer et al. .................... 607/9 |
| 2005/0131476 A1 | 6/2005 | Kim et al. |
| 2005/0137485 A1 | 6/2005 | Cao |
| 2005/0137641 A1 | 6/2005 | Naughton |
| 2005/0192506 A1 | 9/2005 | Kim et al. |
| 2005/0288600 A1 | 12/2005 | Zhang et al. |
| 2006/0069322 A1 | 3/2006 | Zhang et al. |
| 2006/0074331 A1 | 4/2006 | Kim et al. |
| 2006/0111643 A1 | 5/2006 | Cazares et al. |
| 2006/0111747 A1 | 5/2006 | Cazares et al. |
| 2006/0253044 A1 | 11/2006 | Zhang et al. |
| 2006/0259082 A1 * | 11/2006 | Youker et al. ..................... 607/7 |
| 2006/0281998 A1 | 12/2006 | Li et al. |
| 2007/0162414 A1 * | 7/2007 | Horowitz et al. ................. 707/1 |
| 2007/0219456 A1 * | 9/2007 | Thompson .................... 600/518 |

FOREIGN PATENT DOCUMENTS

| | | |
|---|---|---|
| EP | 0547733 | 6/1993 |
| EP | 0801960 | 10/1997 |
| EP | 1267993 | 3/2001 |
| EP | 1112755 | 7/2001 |
| WO | WO0224276 | 3/2002 |
| WO | WO03047690 | 6/2003 |
| WO | WO2006039694 | 4/2006 |

OTHER PUBLICATIONS

Gold et al., "Advanced Rhythm Discrimination for Implantable Cardioverter Defibrillators Using Electrogram Vector Timing and Correlation", Journal of Cardiovascular Electrophysiology, vol. 13, No. 11, Nov. 2002, pp. 1092-1097.

Kerr, "Shock Rate Cut 70% with ICDs Programmed to First Deliver Antitachycardia Pacing: Results of the PainFREE Rx II Trial", NewsRhythms. MedScape CRM News 2003.

(56) References Cited

OTHER PUBLICATIONS

Lake et al., "Sample Antropy Analysis of Neonatal Heart Rate Variability", Am. J. Physiol. Regul. Integr. Comp. Physiol., 283: R789-97 (2002).

Richman et al., "Physiological time-series analysis using approximate entropy and sample entropy", Am. J. Physiol. Heart Circ. Physiol., 278: H2039-49 (2000).

"VITALITY 2 Implantable Cardioverter Defibrillator System Guide", Guidant Corporation, 2004, Cover pages and pp. 3-15 to 3-19.

Wathen et al. "Shock Reduction Using Antitachycardia Pacing for Spontaneous Rapid Ventricular Tachycardia in Patients with Coronary Artery Disease", Circulation 2001, vol. 104:796-801.

Notice of Allowance dated Jan. 11, 2010 from U.S. Appl. No. 11/643,221, 7 pages.

Office Action Response dated Sep. 11, 2009 from U.S. Appl. No. 11/643,221, 15 pages.

Examiner Interview Summary dated Aug. 10, 2009 from U.S. Appl. No. 11/643,221, 2 pages.

Office Action dated Jun. 22, 2009 from U.S. Appl. No. 11/643,221, 13 pages.

Office Action Response dated May 26, 2009 from U.S. Appl. No. 11/643,221, 8 pages.

Office Action dated Apr. 24, 2009 from U.S. Appl. No. 11/643,221, 7 pages.

"U.S. Appl. No. 11/643,221, 312 Amendment filed Apr. 12, 2010", 3 pgs.

"U.S. Appl. No. 11/643,221, Notice of Allowance mailed Jan. 11, 2010", 7 pgs.

"U.S. Appl. No. 11/643,221, PTO Response to 312 Communication mailed Apr. 21, 2010", 2 pgs.

"International Application Serial No. PCT/US2007/019937, International Preliminary Report on Patentability mailed Oct. 30, 2007", 8 pgs.

"International Application Serial No. PCT/US2007/019937, International Search Report mailed Mar. 7, 2008", 2 pgs.

"International Application Serial No. PCT/US2007/019937, Written Opinion mailed Mar. 7, 2008", 6 pgs.

Cazares, Shelley, et al., "U.S. Appl. No. 11/312,280, filed Dec. 20, 2005".

* cited by examiner

| | | | | | Programmed Enhancements | | | | | | | | | | | | |
|---|---|---|---|---|---|---|---|---|---|---|---|---|---|---|---|---|---|
| | | | | | MINI | | | | AV | | | | | | | PZ | AV |
| Detected Rhythm | | | | | V>A=Off, Afib=Off, Stab=Off, Onset=Off | V>A=Off, Afib=Off, Stab=Off, Onset=On | V>A=Off, Afib=Off, Stab=On, Onset=Off | V>A=Off, Afib=Off, Stab=On, Onset=On | V>A=Off, Afib=On, Stab=Off, Onset=Off | V>A=Off, Afib=On, Stab=Off, Onset=On | V>A=Off, Afib=On, Stab=On, Onset=Off | V>A=Off, Afib=On, Stab=On, Onset=On | V>A=On, Afib=Off, Stab=Off, Onset=Off | V>A=On, Afib=Off, Stab=Off, Onset=On | V>A=On, Afib=Off, Stab=On, Onset=Off | V>A=On, Afib=On, Stab=Off, Onset=Off | V>A=On, Afib=On, Stab=On, Onset=On |
| Onset | Stability | A>Afib | V>A | | 1 | 2 | 3 | 4 | 5 | 6 | 7 | 8 | 9 | 10 | 11 | 12 | 13 | 14 |
| Grad | Unstable | T | F | 1 | NA | 1.00 | 1.00 | 1.00 | 1.00 | 1.00 | 1.00 | 1.00 | 1.00 | 1.00 | 1.00 | 1.00 | 1.00 | 1.00 |
| Grad | Unstable | T | T | 2 | NA | 1.00 | 1.00 | 1.00 | 1.00 | 1.00 | 1.00 | 0.10 | 0.10 | 0.10 | 0.10 | 0.10 | 0.10 | 0.10 |
| Grad | Unstable | F | F | 3 | NA | 1.00 | 1.00 | 1.00 | 1.00 | 0.40 | 0.40 | 1.00 | 1.00 | 1.00 | 1.00 | 0.40 | 0.40 | 0.40 |
| Grad | Unstable | F | T | 4 | NA | 1.00 | 1.00 | 1.00 | 1.00 | 0.40 | 0.40 | 0.10 | 0.10 | 0.10 | 0.10 | 0.04 | 0.04 | 0.04 |
| Grad | Stable | T | F | 5 | NA | 1.00 | 0.30 | 0.30 | 0.30 | 0.30 | 0.30 | 1.00 | 0.30 | 0.30 | 0.30 | 1.00 | 0.30 | 0.30 |
| Grad | Stable | T | T | 6 | NA | 1.00 | 0.30 | 0.30 | 0.30 | 0.30 | 0.30 | 0.10 | 0.03 | 0.03 | 0.03 | 0.10 | 0.03 | 0.03 |
| Grad | Stable | F | F | 7 | NA | 1.00 | 0.30 | 0.30 | 0.30 | 0.12 | 0.12 | 1.00 | 0.30 | 0.30 | 0.30 | 0.40 | 0.12 | 0.12 |
| Grad | Stable | F | T | 8 | NA | 1.00 | 0.30 | 0.30 | 0.30 | 0.12 | 0.12 | 0.10 | 0.03 | 0.03 | 0.03 | 0.04 | 0.01 | 0.01 |
| Sud | Unstable | T | F | 9 | NA | 0.20 | 1.00 | 0.20 | 0.20 | 1.00 | 0.20 | 0.20 | 1.00 | 0.20 | 0.20 | 1.00 | 1.00 | 0.20 |
| Sud | Unstable | T | T | 10 | NA | 0.20 | 1.00 | 0.20 | 0.20 | 1.00 | 0.20 | 0.02 | 0.10 | 0.02 | 0.02 | 0.10 | 0.10 | 0.02 |
| Sud | Unstable | F | F | 11 | NA | 0.20 | 1.00 | 0.20 | 0.20 | 0.40 | 0.08 | 0.20 | 1.00 | 0.20 | 0.20 | 0.40 | 0.40 | 0.08 |
| Sud | Unstable | F | T | 12 | NA | 0.20 | 1.00 | 0.20 | 0.20 | 0.40 | 0.08 | 0.02 | 0.10 | 0.02 | 0.02 | 0.04 | 0.04 | 0.01 |
| Sud | Stable | T | F | 13 | NA | 0.20 | 0.30 | 0.06 | 0.06 | 0.30 | 0.06 | 0.20 | 0.30 | 0.06 | 0.06 | 1.00 | 0.30 | 0.06 |
| Sud | Stable | T | T | 14 | NA | 0.20 | 0.30 | 0.06 | 0.06 | 0.30 | 0.06 | 0.02 | 0.03 | 0.01 | 0.01 | 0.10 | 0.03 | 0.01 |
| Sud | Stable | F | F | 15 | NA | 0.20 | 0.30 | 0.06 | 0.06 | 0.12 | 0.02 | 0.20 | 0.30 | 0.06 | 0.06 | 0.40 | 0.12 | 0.02 |
| Sud | Stable | F | T | 16 | NA | 0.20 | 0.30 | 0.06 | 0.06 | 0.12 | 0.02 | 0.02 | 0.03 | 0.01 | 0.01 | 0.04 | 0.01 | 0.00 |

| Assumptions | |
|---|---|
| Probability of Inaccurately Identifying VT | |
| V > A | 0.10 |
| Afib | 0.40 |
| Stability | 0.30 |
| Onset | 0.20 |
| All Treat | 0.00 |
| Enhancement = false | 1.00 |
| Enhancement = off | NA |

Treat Rule (per column): Always Trt; Sudden; Stable; Sudden and Stable; Sudden or Stable; A<Afib or Stable; (Stbl and Sud) or (Stbl and A<Afib) or (Sud and A<Afib); V>A or Sudden; V>A or Stable; V>A or (Sudden and Stable); V>A or Sudden or Stable; V>A or A<Afib; V>A or A<Afib or Stable; V>A or (Stbl and Sud) or (Stbl and A<Afib)

| Detected Rhythm | | | | VTI | Current Treat Decision | OBDEs Voting Treat |
|---|---|---|---|---|---|---|
| Onset | Stability | A > Afib | V>A | | | |
| Sud | Stable | F | T | 0.00 | Trt | 4 |
| Sud | Stable | T | T | 0.01 | Trt | 3 |
| Sud | Unstable | F | T | 0.01 | Trt | 3 |
| Grad | Stable | F | T | 0.01 | Trt | 3 |
| Sud | Unstable | T | T | 0.02 | Trt | 2 |
| Sud | Stable | F | F | 0.02 | Trt | 3 |
| Grad | Stable | T | T | 0.03 | Trt | 2 |
| Grad | Unstable | F | T | 0.04 | Trt | 2 |
| Sud | Stable | T | F | 0.06 | Trt | 2 |
| Sud | Unstable | F | F | 0.08 | | 2 |
| Grad | Unstable | T | T | 0.10 | Trt | 1 |
| Grad | Stable | F | F | 0.12 | | 2 |
| Sud | Unstable | T | F | 0.20 | | 1 |
| Grad | Stable | T | F | 0.30 | | 1 |
| Grad | Unstable | F | F | 0.40 | | 1 |
| Grad | Unstable | T | F | 1.00 | | 0 |

Region "A"
Region "B"
Region "C"

Figure 2C

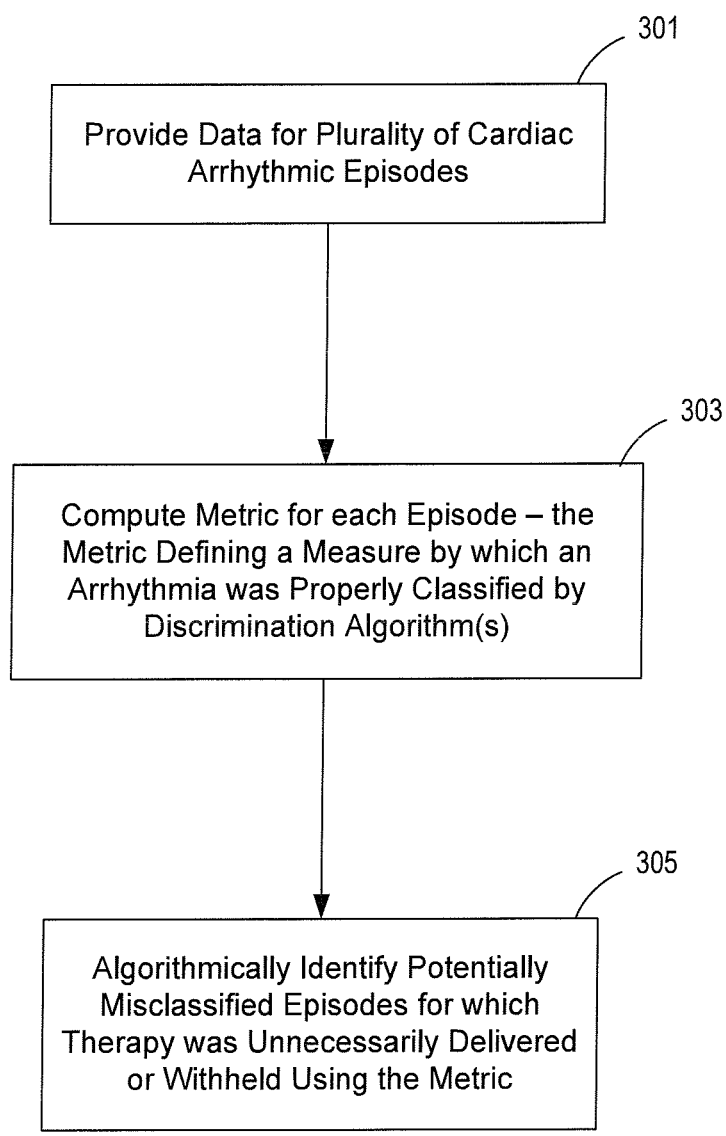

METHOD AND APPARATUS FOR IDENTIFYING POTENTIALLY MISCLASSIFIED ARRHYTHMIC EPISODES

RELATED APPLICATIONS

This application is a continuation of U.S. Pat. No. 7,738,950, and claims the benefit of Provisional Patent Application Ser. No. 60/844,253, filed on Sep. 13, 2006, which are hereby incorporated herein by reference.

FIELD OF THE INVENTION

The present invention relates generally to cardiac systems and methods, and, more particularly, to systems and method for identifying cardiac arrhythmias that are potentially misclassified.

BACKGROUND OF THE INVENTION

Proper cardiac function relies on the synchronized contractions of the heart at regular intervals. When normal cardiac rhythm is initiated at the sinoatrial node, the heart is said to be in sinus rhythm. However, due to electrophysiologic disturbances caused by a disease process or from an electrical disturbance, the heart may experience irregularities in its coordinated contraction. In this situation, the heart is denoted to be arrhythmic. The resulting cardiac arrhythmia impairs cardiac efficiency and can be a potential life threatening event.

Cardiac arrhythmias occurring in the atria of the heart, for example, are called supra-ventricular tachyarrhythmias (SVTs). SVTs take many forms, including atrial fibrillation and atrial flutter. Both conditions are characterized by rapid, contractions of the atria. Cardiac arrhythmias occurring in the ventricular region of the heart, by way of further example, are called ventricular tachyarrhythmias. Ventricular tachyarrhythmias (VTs), are conditions denoted by a rapid heart beat, 150 to 250 beats per minute, originating from a location within the ventricular myocardium. Ventricular tachyarrhythmia can quickly degenerate into ventricular fibrillation (VF). Ventricular fibrillation is a condition denoted by extremely rapid, non synchronous contractions of the ventricles. This condition is fatal unless the heart is returned to sinus rhythm within a few minutes.

Implantable cardioverter/defibrillators (ICDs) have been used as an effective treatment for patients with serious tachyarrhythmias. ICDs are able to recognize and treat tachyarrhythmias with a variety of tiered therapies. These tiered therapies range from providing anti-tachycardia pacing pulses or cardioversion energy for treating tachyarrhythmias to high energy shocks for treating ventricular fibrillation. To effectively deliver these treatments, the ICD must first identify the type of tachyarrhythmia that is occurring, after which appropriate therapy may be provided to the heart.

For the reasons stated above, and for other reasons stated below which will become apparent to those skilled in the art upon reading the present specification, there is a need in the art for reliably and accurately recognize types of cardiac rhythms produced by the heart. The present invention fulfills these and other needs.

SUMMARY OF THE INVENTION

The present invention is directed to methods and systems for identifying cardiac arrhythmias that are potentially misclassified. According to various embodiments, methods and systems of the present invention provide for identification of cardiac arrhythmias that are potentially misclassified by a cardiac device implanted in a patient. The implantable cardiac device is configured to classify cardiac arrhythmias using a number of arrhythmia discrimination algorithms. Data is provided that is associated with a number of cardiac arrhythmic episodes for which a cardiac electrical therapy was delivered or withheld by the implantable cardiac device based on the arrhythmia discrimination algorithms.

A metric is computed for each of the arrhythmic episodes. The metric defines a measure by which the implantable cardiac device properly classified the arrhythmia. Methods and system further provide for algorithmically identifying potentially misclassified arrhythmic episodes of the cardiac arrhythmic episodes for which cardiac electrical therapy was inappropriately delivered or withheld using the metric. Algorithmically identifying potentially misclassified arrhythmic episodes may involve comparing metric values of the cardiac arrhythmic episodes to a threshold or a threshold range.

The metric may define a probability of incorrectly classifying a cardiac arrhythmic episode, such as a probability of incorrectly classifying a ventricular tachycardia episode. The metric may be reflective of the accuracy by which each arrhythmia discrimination algorithm implemented by the implantable cardiac device properly classified an arrhythmic episode. The metric may be based on a product of the probabilities of the arrhythmia discrimination algorithms implemented by the implantable cardiac device to incorrectly classify an arrhythmic episode.

The data and metrics associated with the cardiac arrhythmic episodes may be arranged in a logbook format. The potentially misclassified arrhythmic episodes may be displayed for clinician review. For example, the data may be sorted based on the metrics, and the sorted data and metrics may be displayed for clinician review. The manner in which the data and metrics associated with the potentially misclassified arrhythmic episodes are displayed may be varied in accordance with a degree of potential misclassification.

Computing the metric and algorithmically identifying potentially misclassified arrhythmic episodes may be respectively performed by a device external to the patient. For example, the data may be provided to a processor external of the patient. The external processor may implement one or more arrhythmia discrimination algorithms to classify the cardiac arrhythmias based on the data. The metric may represent a measure of certainty that the cardiac arrhythmia classification of arrhythmic episodes respectively made by the implantable cardiac device and the external processor are in agreement.

Methods and systems may provide for adjustment of the metric in response to clinician input and/or adjusting a parameter of one or more of the arrhythmia discrimination algorithms. Arrhythmic episodes may be flagged for clinician review in response to the metric failing to exceed a certainty threshold. One or more of the arrhythmia discrimination algorithms of the implantable cardiac device may be modified in response to the metric failing to exceed a certainty threshold.

In some implementations, the arrhythmia discrimination algorithms may include an algorithm that compares a morphology of a cardiac signal to a supraventricular tachycardia (SVT) template. An SVT template may be automatically generated for arrhythmic episodes for which the cardiac arrhythmia classifications respectively made by the implantable cardiac device and the external processor are in disagreement but the metric meets or exceeds a certainty threshold.

In other implementations, the arrhythmia discrimination algorithms may include an algorithm that compares a morphology of a cardiac signal to a supraventricular tachycardia (SVT) template. Arrhythmic episodes for clinician review may be flagged in response to the metric failing to meet or exceed a certainty threshold. An SVT template may be generated for selected ones of the flagged arrhythmic episodes in response to a clinician input.

Systems of the present invention may include an implantable cardiac device configured to classify cardiac arrhythmias using a number of arrhythmia discrimination algorithms. A memory preferably stores data associated with a number of cardiac arrhythmic episodes for which a cardiac electrical therapy was delivered or withheld by the implantable cardiac device based on the arrhythmia discrimination algorithms.

A processor may be configured to compute a metric for each of the arrhythmic episodes, the metric defining a measure by which the implantable cardiac device properly classified the arrhythmia. The processor may be configured to algorithmically identify potentially misclassified arrhythmic episodes of the cardiac arrhythmic episodes for which cardiac electrical therapy was inappropriately delivered or withheld using the metric. In some implementations, one or both of the memory and processor is disposed in the implantable cardiac device. In other implementations, one or both of the memory and processor is disposed in a patient-external device.

The above summary of the present invention is not intended to describe each embodiment or every implementation of the present invention. Advantages and attainments, together with a more complete understanding of the invention, will become apparent and appreciated by referring to the following detailed description and claims in conjunction with the accompanying drawings.

BRIEF DESCRIPTION OF THE DRAWINGS

FIG. 2A is a treatment decision table arranged in a conventional manner for use by an implantable cardiac device;

FIG. 2B is a treatment decision table arranged based on validation metric values for use by an implantable cardiac device or an external processor in accordance with embodiments of the present invention;

FIG. 2C is a partial showing of an arrhythmia logbook report with data presented based on a validation metric sort in accordance with embodiments of the present invention;

FIG. 3 is a flow chart that characterizes a validation metric-based discrimination algorithm of the present invention;

Figure 1A:
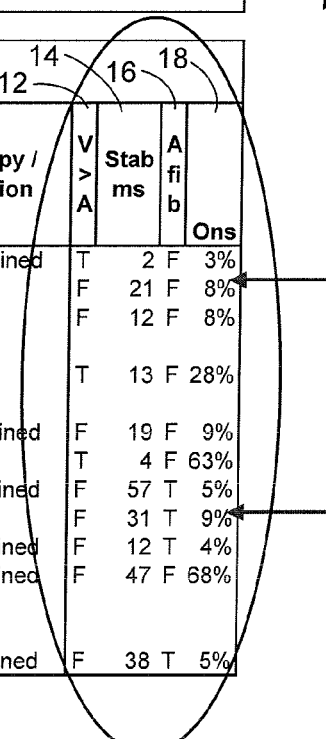
FIG. 1A shows a typical report of an arrhythmia logbook that presents various data associated with a number of arrhythmic episodes.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

Description of Various Embodiments

In the following description of the illustrated embodiments, references are made to the accompanying drawings forming a part hereof, and in which are shown, by way of illustration, various embodiments by which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described herein. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

The present invention is directed to methods and systems for analyzing data associated with cardiac rhythms and, in particular, cardiac arrhythmias such as tachycardia. Methods and systems of the present invention may be implemented to analyze cardiac rhythm data for assessing whether an arrhythmic episode, such as a tachycardia episode, has been properly classified. Methods and systems of the present invention may be implemented to analyze cardiac rhythm data for assessing whether a cardiac therapy delivered to, or inhibited from, a patient was appropriate. Such analyses may be performed by an implantable device, an external device, or a combination of both, fully automatically or with assistance/input from a clinician or physician.

Analysis results may be used to modify device parameters that influence diagnosis and/or treatment of cardiac arrhythmias by the implantable device. Such modifications may be implemented autonomously (i.e., algorithmically) without user input or may involve input from a user. Analyses and modification to device parameters may be performed within an implantable device, by a processing device external to the patient, or a combination of both.

According to embodiments of the invention, the complexity associated with conventional methods of analyzing cardiac rhythm data by a user is significantly reduced by implementation of a validation metric. A validation metric of the present invention may be used in a variety of applications, including verification of device diagnostics and therapy decisions, troubleshooting and modifying device diagnostics and therapies, triggering initiation of diagnostics and/or therapies, and remote system/user reporting and alerting function, among others.

A validation metric of the present invention represents an easily understandable index that may be used to assess (e.g., filter) the very detailed information obtained by diagnostic algorithms operative in most implantable cardiac devices. In particular embodiments, a validation metric represents a measure by which an implantable cardiac device properly classified an arrhythmia. A validation metric may be used to identify potentially misclassified arrhythmias for which cardiac electrical therapy was improperly delivered or withheld. A validation metric of the present invention may be used by an implantable cardiac device for making therapy decisions.

Features and advantages of a validation metric of the present invention can be readily appreciated in the context of cardiac rhythm data that is stored or presented in a tabular or matrix format, such as a logbook format as is known in the art. It is understood that a validation metric of the present invention may be used in a variety of manners, and that use in the context of an arrhythmia logbook represents one of many such applications. For example, and as will be discussed hereinbelow, a validation metric or other validation algorithm may be implemented by a patient-external processing system to verify the appropriateness of arrhythmia classifications made by an implantable cardiac device, and to enhance arrhythmia discrimination and therapy delivery performance.

FIG. 1A shows a typical report 10 of an arrhythmia logbook that presents various data associated with a number of arrhythmic episodes. The data in FIG. 1A is sorted in a traditional manner by date and time of the arrhythmic episode. In the data shown in FIG. 1A, the implantable cardiac device from which the data was obtained implemented a number of different algorithms when discriminating between normal and arrhythmic cardiac rhythms, four of which are shown in FIG. 1A. In the particular example illustrated in FIG. 1A, data associated with four discrimination algorithms is provided in columns 12, 14, 16, and 18.

The first column 12 of discriminator data represents a Boolean output (True "T" or False "F") from a "V>A" discriminator, which compares ventricular and atrial rates to determine if the ventricular rate exceeds the atrial rate plus a bias factor, such as 10 bpm. The second column 14 of discriminator data represents the stability of a ventricular rhythm, which is shown in terms of milliseconds. The third column 16 of discriminator data represents a Boolean output from an "A>Afib" discriminator, which compares the atrial rate to an atrial fibrillation threshold, such as 200 bpm for example. This discriminator is used to inhibit therapy when a ventricular tachycardia is due to atrial fibrillation. The fourth column 18 of discrimination data represents the onset character of a ventricular cardiac rhythm, such as sudden or gradual onset, and is used to differentiate sinus tachycardia from ventricular tachycardia. This data is represented in terms of a percentage.

The discriminators and associated data depicted in FIG. 1A are representative of known algorithms that are used to evaluate cardiac arrhythmias and identify arrhythmic episodes that require therapy. It is understood that many other discriminators known in the art may be employed in an implantable cardiac device and that a validation metric and methods of using same in accordance with the present invention may be implemented in an implantable cardiac device that employs such other known discriminators. A validation metric and methods of using same in accordance with the present invention may also be employed in patient-external devices and systems that operate on data associated with various known discriminators.

Figure 2A:
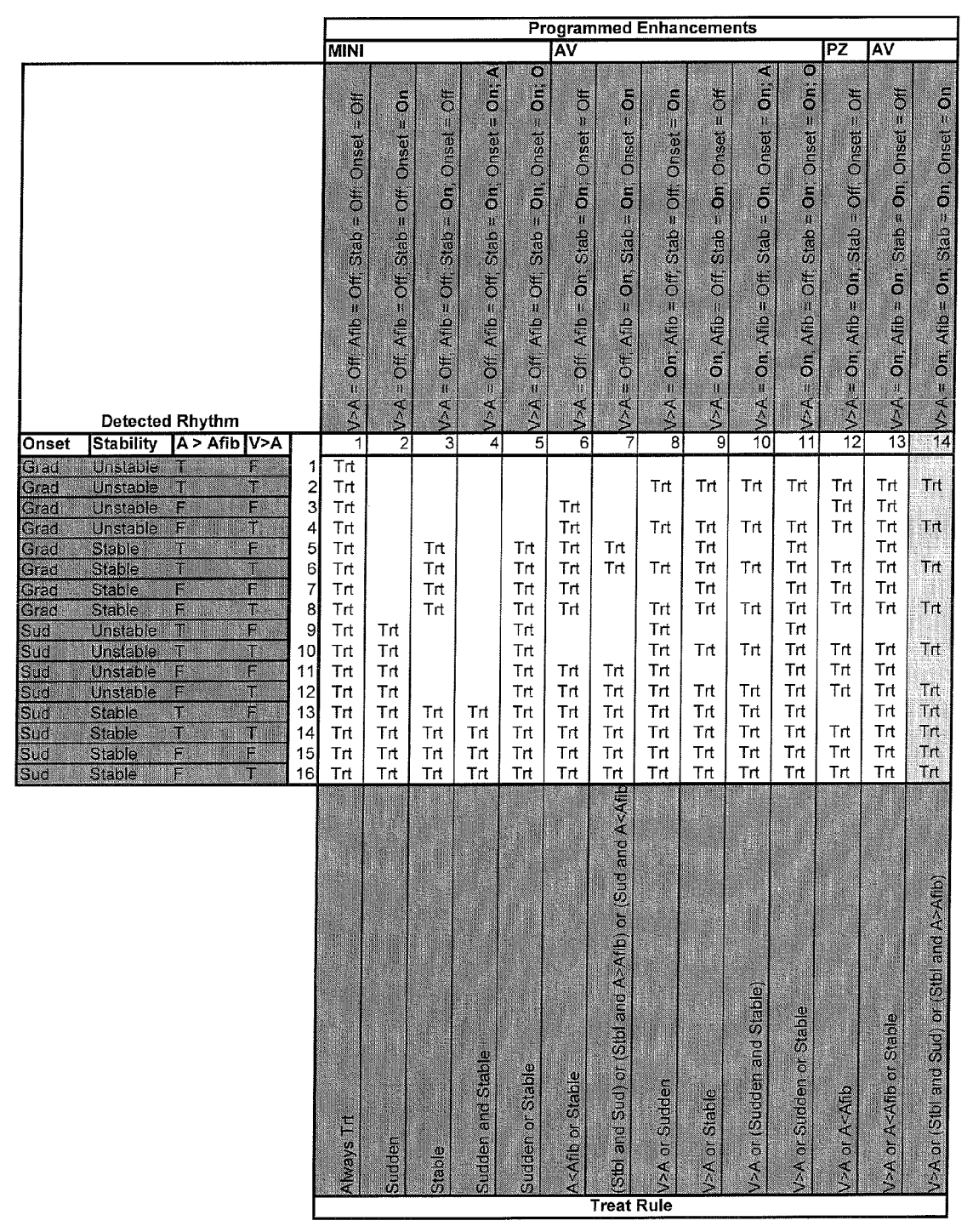

In addition to assessing the data associated with the four discriminators shown in FIG. 1A, the state of programmable settings of such discriminators when the data was acquired is also important. As is shown in FIG. 2A, each of the four discriminators whose data is shown in FIG. 1A can be programmed OFF or ON, and each typically has a range of programmable setting values. FIG. 2A is a device treatment decision table which is a mapping of discriminator activation state (shown along upper horizontal side), discriminator outcome state (shown along left vertical side), and treatment rules (shown along lower horizontal side).

When attempting to evaluate cardiac arrhythmia data, a clinician is typically provided with a list of episodes on an arrhythmia logbook report retrieved from an implantable cardiac device by way of a programmer, as is shown in FIG. 1A. This list is typically organized by date and type of episode. Columns may also be provided that display the highest rate achieved during an episode and whether therapy was delivered. While this information presents a helpful snapshot of the patient's episode history, date, type, and high rate, such information is typically not sufficient to expeditiously prioritize the list for assessing device functionality and patient arrhythmia classifications. Additionally, for patients with multiple treated episodes, the indication of treatment also does not facilitate episode prioritization.

More detailed information concerning an episode is typically provided on an episode detail report. This report presents the calculations associated with each discriminator. Analyzing this very detailed information is often helpful when deciding to fully investigate a specific episode. However, such detailed information does not assist the clinician in identifying which episodes should be selected to best assess the device and the patient. In a typical follow-up clinical setting, a clinician (e.g., a physician and/or device manufacturer representative) are often time-constrained by limited patient visits which are typically scheduled 15 minutes apart, making a thorough evaluation of each arrhythmic event impractical.

In the absence of information that would enable a clinician to prioritize a list of arrhythmia episodes, many clinicians, who do not systemically check each episode, randomly select a few episodes to investigate. Random selection, as a method, has been found to be generally effective in the field, and, as a result, is widely practiced. However, random selection processes, by definition, can often result in overlooking episodic data of importance, which may go unevaluated.

It can be appreciated that assessing cardiac rhythms based on multiple discriminator data and programmable device settings can be relatively complex and time consuming, particularly when evaluating such data during routine follow-up patient visits of limited duration with a clinician. Ironically, although increases in device sophistication has generally led to improved diagnosis and treatment of cardiac arrhythmias, such increased sophistication has made it more difficult and time consuming for the clinician to evaluate the appropriateness of device functionality and decision-making processes.

A validation metric of the present invention represents a single index that can be used to rapidly identify possibly misclassified tachycardia episodes. For example, a validation metric value falling within a predetermined range or exceeding a predetermined threshold can be used to identify tachycardia episodes that require evaluation, and prompt the clinician to further investigate such episodes. A validation metric of the present invention effectively reveals the level of confidence that the implantable cardiac device properly classified detected cardiac arrhythmias. A validation metric can serve to help the clinician prioritize episodes for troubleshooting and to more quickly and accurately determine the operating status/proper functionality of the device and the patient's clinical event history. A validation metric can also be used to validate device diagnoses and the appropriateness of therapy decisions. In this regard, a validation metric can effectively verify that the rhythm discriminator algorithms implemented in a particular implantable cardiac device are properly classifying cardiac arrhythmias.

According to various embodiments, a validation metric of the present invention defines a probability of incorrectly classifying a cardiac arrhythmic episode, such as a ventricular tachycardia episode, as one that requires treatment. A validation metric is reflective of the accuracy by which each arrhythmia discrimination algorithm implemented by an implantable cardiac device properly classified an arrhythmic episode. For example, a validation metric is preferably based on a product of the probabilities of the arrhythmia discrimination algorithms implemented by an implantable cardiac device to incorrectly classify an arrhythmic episode. Identifying potentially misclassified arrhythmic episodes typically involves comparing validation metric values of classified cardiac arrhythmic episodes to a threshold or a threshold range.

By way of example, a validation metric of the present invention may be computed based on the probability that an arrhythmia discriminator is satisfied as "treat for ventricular tachycardia," but the underlying rhythm is actually supraventricular tachycardia (SVT) or is distorted by noise. The probability of inaccurately identifying ventricular tachycardia (VT) for a given discrimination algorithm can be expressed as:

Probability of inaccurately identifying VT=1−(probability of accurately identifying VT)

For example, if a given arrhythmia discriminator has a probability of 85% for accurately identifying a rhythm as VT, then it also has a 15% probability (i.e., 1−0.85=0.15) of inaccurately identifying the rhythm as VT. This 15% probability accounts for device errors due to well documented and understood sources, such as electrogram noise. A validation metric is preferably calculated by taking the individual probabilities of each arrhythmia discrimination algorithm employed by the implantable cardiac device and multiplying these probabilities to produce a combined probability.

Conventional discrimination algorithms generally rely on thresholds (e.g., all-or-nothing scenarios such as whether or not the atrial rate is >200 bpm) to classify rhythms and/or the application/inhabitation of therapy. In contrast, a validation metric of the present invention represents a quantitative measure of device confidence in its rhythm classification and/or therapy decisions based on a dynamic range of probabilities derived from a continuum of discriminator output values.

FIG. 2B shows a device treatment decision table similar to that of FIG. 2A. However, the treatment decision matrix of FIG. 2A has been replaced with a matrix of validation metrics. As can be seen in FIG. 2B, the more arrhythmia discriminator algorithms that are satisfied by the rhythm detected by the device, the lower the validation metric value will become. The lower the value of the validation metric, the lower the probability that the device has inaccurately identified ventricular tachycardia. In other words, one can be increasingly confident of the device's determination of ventricular tachycardia and its administration of therapy as the metric value becomes lower.

Figure 1B:
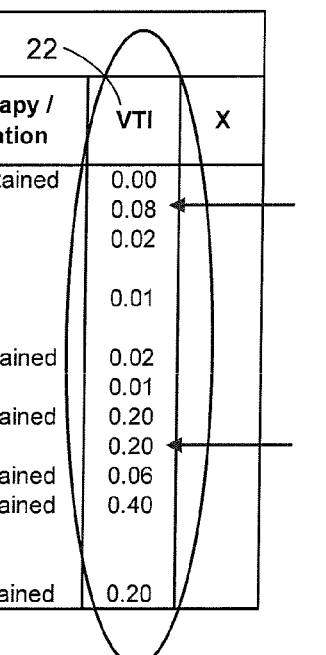
FIG. 1B shows a report of an arrhythmia logbook that presents various cardiac rhythm data and a validation metric associated with each of the arrhythmic episodes in accordance with embodiments of the present invention.

FIG. 1B shows a report 20 of an arrhythmia logbook that presents various cardiac rhythm data and a validation metric associated with each of the arrhythmic episodes shown in report 20. As is readily seen by a comparison of the reports 10 and 20 shown in FIGS. 1A and 1B, respectively, presentation of a single validation metric (shown in column 22 as VTI or ventricular tachycardia index), in contrast to the multiplicity of columnar data for four discriminators, greatly simplifies the characterization of each arrhythmic episode. The data presented in the report 20 may be sorted based on validation metric values to allow for quick identification of episodic data requiring further evaluation by a clinician.

FIG. 2C is a partial showing of an arrhythmia logbook report 20 with data presented based on a validation metric sort. The data of column 24 of report 20 represents validation metric values computed for each row of arrhythmic episode data shown in report 20. Column 26 represents the "treat" (trt) or "no-treat" (blank) decision made by use of a conventional treatment decision table, such as that shown in FIG. 2A. Column 28 represents the outcome of voting to treat (i.e., voting to deliver therapy) by each of the four discriminators depicted in FIG. 2C. For example, a vote value of 3 indicates that 3 of the 4 discriminators voted to treat the subject arrhythmia. The decision to treat or inhibit treatment is typically based on a weighted voting scheme.

As is discussed above, lower validation metric values are indicative of higher probabilities that the device correctly classified a cardiac arrhythmia for treatment. In general, validation metric values lower than about 0.10 indicate a relatively high probability that the device correctly classified a cardiac arrhythmia. Validation metric values in excess of about 0.10 indicate a relatively higher probability that the device may have incorrectly classified a cardiac arrhythmia. For example, episodes having metric values in excess of 0.20 that were indicated as treated by the device are possible candidates of false positive assessments made by the device.

The validation metric data in region A of report 20 indicates that the episodes are likely appropriately classified, and that treatment of same was appropriate. It can be seen that the validation metric values in column 24 of region A are relatively low, indicating a relatively high probability that the device properly classified the cardiac rhythm. The voting data in column 28 of region A corroborates this outcome. The current treatment decision data in column 26 of region A indicates that therapy was properly delivered to treat each of the arrhythmias associated with the region A data.

The validation metric values in column 28 of region B are greater than those in region A, indicating an increased likelihood that the device may have improperly classified a given rhythm. In general, the validation metric values in region B are relatively low. However, the voting data in column 28 for region B indicates a reduced number of votes to treat. A review of the data in region B suggests that one of the rhythms (the rhythm having a validation metric value of 0.10 and voting value of 1) for which treatment was delivered is quite likely suspect—a likely false positive. This rhythm has an indication of treatment delivery with a relatively high validation metric value, and likely represents a borderline scenario for treatment which warrants further investigation.

Region B is populated by data for several episodes that have relatively increased validation metric values, a reduced number of votes to treat as can be seen in column 28, and an indication of treatment delivery. These episodes in region B are good candidates for further evaluation of device functionality and/or decision making criteria.

The data in region C reveals relatively high validation metric values in column 24 for rhythms that were not subject to treatment. Because the higher validation metric values indicate an increasing probability that the device improperly classified the rhythms in region C, these episodes would warrant further investigation if there were a corresponding indication of treatment delivery in column 26. In the illustrative example shown in FIG. 2C, none of the episodes in region C were subject to treatment, and, therefore, would not necessarily be of particular interest for further evaluation.

The data shown in FIG. 2C illustrates how a validation metric can be used to facilitate rapid evaluation of data for a large number of arrhythmic episodes. A validation metric of the present invention reveals which episodes should be subject to further evaluation by a clinician and does so in a manner that is easily perceptible and readily understandable. To increase data perception, colors or other indicia may be incorporated into the data presentation. For example, the regions shown in FIG. 2C may be colorized in a manner that connotes their relative probability of classification accuracy. For example, region A may be colored "green" to indicate episodes that are likely properly classified. Region B may be colored "yellow" to indicate episodes that may necessitate further review, particularly those that have an indication of therapy delivery. Region C may be colored "red" to indicate episodes that require further investigation where there is an indication of treatment delivery for such episodes.

A validation metric approach of the present invention may be used in current and future cardiac devices that use a multiplicity of rhythm discrimination or classification algorithms. Validation metric values can be added to diagnostic and therapy evaluation reports, such as a column on an arrhythmia logbook report, and could replace the multiplicity of columnar data currently occupied by individual discriminator data. Accordingly, clinicians could be exposed to the detail of the multiplicity of discriminator data after the validation metric has guided them to the potentially problematic episodes. Since the validation metric effectively incorporates multiple columns of discriminator data into a single column, it has the potential to be quickly and widely used since clinicians are likely to readily understand what the metric is attempting to demonstrate, particularly to less sophisticated clinicians.

According to one implementation, a validation metric-based discrimination algorithm is initially available on an external processor or system, such as a programmer or a remote server-based APM system. The validation metric-based discrimination algorithm may be transferred from the external processor/system to the implantable cardiac device. Thereafter, the processor of the implantable device may implement the validation metric-based discrimination algorithm. It is understood that the validation metric-based discrimination algorithm may be implemented by the external system only, by the implantable cardiac device only or, preferably, by both the patient-internal and patient-external devices/systems.

FIG. 3 is a flow chart that provides a general characterization of a validation metric-based discrimination algorithm of the present invention. Data for a number of cardiac arrhythmic episodes are provided 301 to the processor of the implantable cardiac device or an external processor, such as that of a programmer or an APM system. A validation metric is computed 303 for each episode. As discussed above, the validation metric represents a measure by which an arrhythmia was properly (or improperly) classified by the discrimination algorithms implemented by the implantable cardiac device. Potentially misclassified episodes are algorithmically identified 305 to assess whether delivery of therapy or withholding of same was proper or improper.

The outcome from this assessment may be used to trigger additional processes, such as modification of a therapy parameter or generation of a template in the context of a morphology-based discrimination algorithm. The outcome from this assessment may also be used for various alerting and reporting functions, such as notifying a physician of discordance between classifications made by the implantable device and external device, respectively. These and other processes may be implemented automatically, by the physician, or by cooperation of automatic and physician-assisted processes.

A validation metric of the present invention may be used in a variety of manners, including validation of implantable cardiac device classification and/or therapy decisions by an external system. Many implantable medical devices employ multiple detection algorithms to enhance classification of cardiac rhythms. The sophistication of such detection algorithms is typically limited by the computational resources of the implantable cardiac device. This computational limitation can be offset by use of virtually unlimited computational resources of systems available externally of the patient.

Due to limited computations resources, conventional tachyarrhythmia detection algorithms have used rate, stability, and onset to discriminate between ventricular tachycardia (VT) and supraventricular tachycardia (SVT). Morphology-based algorithms represent an improvement on these conventional algorithms, but make the assumption that arrhythmias not originating in the ventricle have electrogram morphologies similar to conducted normal sinus rhythm, which may or may not be accurate. The addition of physician-identified SVT templates for morphology-based detection algorithms has been shown to improve morphology-based rhythm identification (RID) algorithm performance, but results in increased physician burden. Use of a validation metric of other validation algorithm may be used to automate SVT template generation using patient-external computing resources, such as remote APM systems.

Figure 4B:
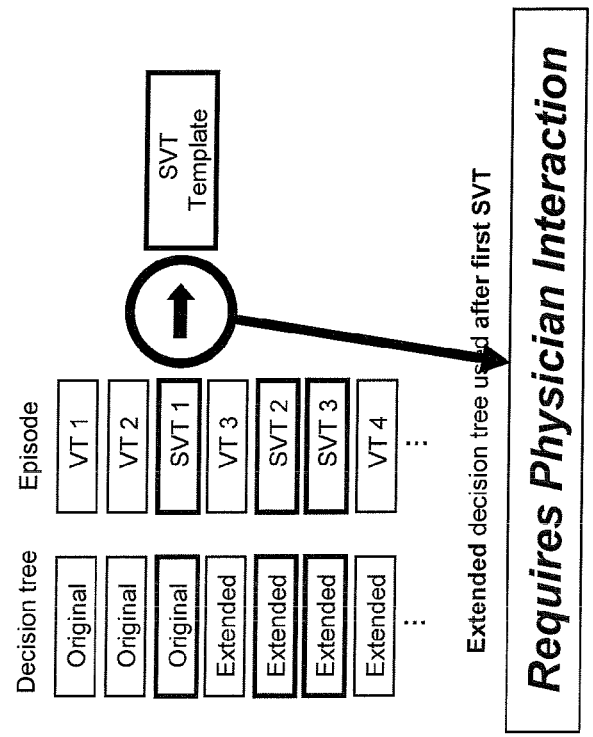
FIG. 4B describes various operations performed by the morphology-based rhythm identification algorithm shown in FIG. 4A.
Figure 4A:
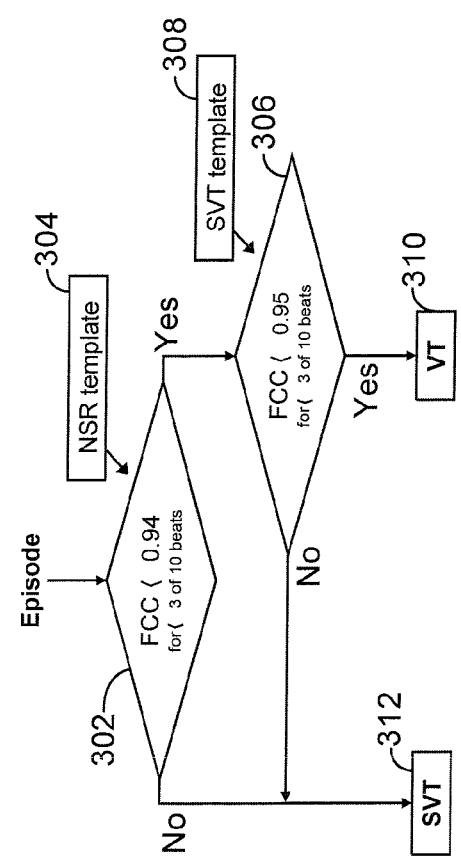
FIG. 4A is a flow chart that characterizes a morphology-based rhythm identification algorithm according to embodiments of the present invention.

FIG. 4A is a flow chart that characterizes a morphology-based rhythm identification algorithm according to embodiments of the present invention. According to this embodiment, two types of morphological templates are used to evaluate cardiac rhythms. A first routine of the algorithm shown in FIG. 4A compares cardiac rhythms to an NSR (normal sinus rhythm) template 304. Such an NSR template is typically generated by the implantable cardiac device, and may be updated over time.

A second routine of the algorithm shown in FIG. 4A compares cardiac rhythms to one or more SVT templates 308. Such SVT templates 308 are typically generated in response to physician analysis of device data. The physician is typically required to review stored electrograms that have a supraventricular origin, and determine if indeed such electrograms are representative of SVT rhythms. The physician may then initiate generation of an SVT template, via a programmer or APM system, which is subsequently transferred to the implantable cardiac device. The SVT template may then be used in the second comparison routine shown in boxes 306, 308 in FIG. 4A. FIG. 4B depicts the use of physician-generated SVT templates in an extended decision tree that is enabled after a first physician-generated SVT template is transferred to the implantable cardiac device.

With continued reference to FIG. 4A, arrhythmic episodes are detected by the implantable cardiac device, and a number of morphological features of each beat are compared to an NSR (normal sinus rhythm) template 304. Comparisons are made between each feature of a given beat and a corresponding feature of the NSR template 304. A mathematical correlation coefficient, referred to as a feature correlation coefficient (FCC), is computed for the features of each beat. If a sufficient number of beats in a sequence of beats have FCC values that exceed a predefined threshold (e.g., FCC not <0.94 or, in other words, FCC≥0.94), as tested at box 302, then the rhythm is classified as an SVT rhythm 312.

If a sufficient number of beats in a sequence of beats have FCC values that fail to exceed a predefined threshold (e.g., FCC<0.94), as tested at box 302, then a secondary or extended evaluation of the rhythms is made using an SVT template 308. It is assumed that SVT template 308 was generated by a physician and transferred to the implantable cardiac device in a manner discussed above. If a sufficient number of beats in a sequence of beats have FCC values that exceed a predefined threshold (e.g., FCC not <0.95 or, in other words, FCC≥0.95), as tested at box 306, then the rhythm is classified as an SVT rhythm 312. If, however, a sufficient number of beats in a sequence of beats have FCC values that fail to exceed a predefined threshold (e.g., FCC<0.95), as tested at box 306, then the rhythm is classified as a VT rhythm 310.

A morphology-based detection approach, such as that shown in FIGS. 4A and 4B, and as discussed above, may be implemented in accordance with the disclosures of commonly owned U.S. Pat. Nos. 7,277,747; 7,894,893; 7,653,431 and 6,449,503, all of which are hereby incorporated herein by reference.

Figure 5:
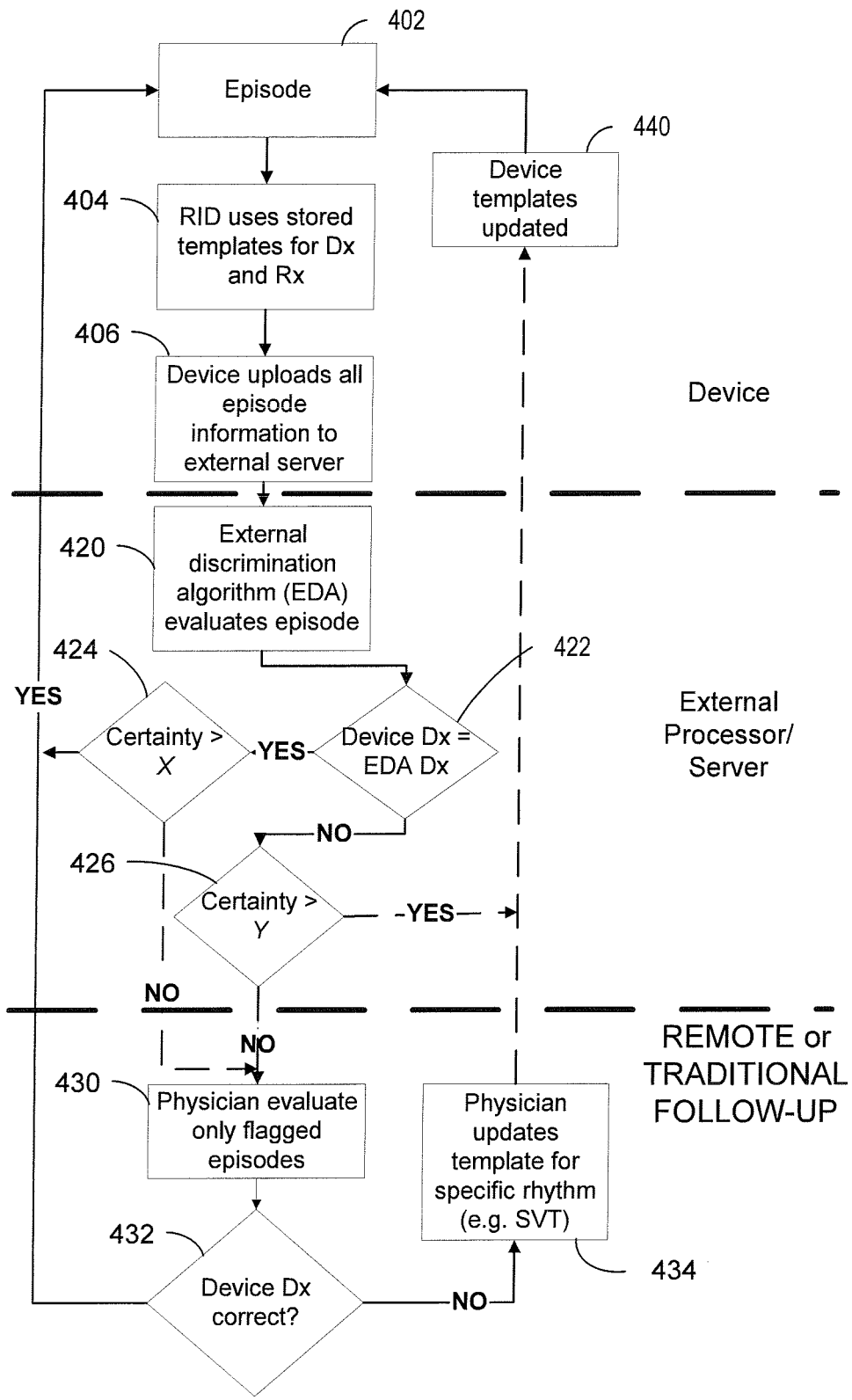
FIG. 5 illustrates a method of improving the performance of a morphology-based tachyarrhythmia discrimination algorithm implemented by an implantable cardiac device by use of patient-external computational resources in accordance with embodiments of the present invention.

FIG. 5 illustrates a method of improving the performance of a morphology-based tachyarrhythmia discrimination algorithm implemented by an implantable cardiac device by use of patient-external computational resources. According to the embodiment shown in FIG. 5, arrhythmic episodes are evaluated 402, 404 by use of a morphology-based tachyarrhythmia discrimination algorithm, shown as a rhythm identification algorithm. As previously discussed, the RID algorithm uses NSR and SVT templates 404 for diagnosis of arrhythmias and treatment of same. Following a tachyarrhythmia event, the implantable cardiac device uploads 406 all relevant data for the event to an external processor or server (e.g., an APM system processor/server). The relevant data may include electrograms from all available channels (e.g., right atrium, right ventricle, shock or far-field channels) and timing information (e.g., rate, stability, onset).

An external discrimination algorithm (EDA) is implemented by the external system (e.g., APM server) to evaluate 420 the arrhythmic event or episode. The EDA is preferably a blinded algorithm implemented by the APM server to analyze and classify the rhythms implicated in the uploaded data. Preferably, all arrhythmic events are recorded and stored on the APM server.

If the discrimination algorithm implemented on the APM server is the same algorithm as used in the implantable cardiac device, the event is noted as such. It is desirable to use a discrimination algorithm that differs from those employed by the implantable cardiac device. In one embodiment, for example, the EDA is implemented using a validation metric methodology described hereinabove.

In another embodiment, the EDA is implemented as an enhanced rhythm identification discrimination algorithm. In general, the number of electrogram features subject to FCC analysis by the implantable cardiac device is limited by the limited computational resources of the implantable device platform. A typical RID analysis involves comparison of some 8 or 10 morphological features for detected electrogram waveforms and VT and/or SVT templates. An EDA analysis need not be limited to the number of features analyzed by the implantable cardiac device. For example, the EDA analysis may involve in excess of 20 morphological features, such as up to 100 or more features.

Moreover, more sophisticated and/or computationally intensive correlation techniques may be employed by the EDA (or plural EDAs) to increase the probability of properly classifying a given rhythm by the EDA. Other discrimination algorithms in addition to RID may be implemented as EDAs to verify or corroborate the outcome of rhythm assessments by RID or other primary discrimination algorithm(s). Such other discrimination algorithms may include rate-based, pattern-based, or rate and pattern-based discrimination algorithms as are known in the art. Each of these discrimination algorithms may be modified to enhance rhythm classification robustness in view of the virtually unlimited computational resources made available by external systems.

According to a further embodiment, the EDA may be implemented to perform wavelet analysis when comparing detected rhythm waveforms and template waveforms. For example, digitized cardiac signals may be analyzed by first transforming the signals into signal wavelet coefficients using a wavelet transform. Higher amplitude signal wavelet coefficients may be identified and compared with a corresponding set of template wavelet coefficients derived from signals indicative of a heart depolarization of known type (e.g., NSR, VT, SVT templates/signals). The digitized signals may be transformed using a Haar wavelet transform to obtain the signal wavelet coefficients, and the transformed signals may be filtered by deleting lower amplitude signal wavelet coefficients.

The transformed signals may be compared by ordering the signal and template wavelet coefficients by absolute amplitude and comparing the orders of the signal and template wavelet coefficients. Alternatively, the transformed signals may be compared by calculating distances between the signal and wavelet coefficients. Details of suitable wavelet analysis techniques that may be implemented by an EDA of the present invention are disclosed in U.S. Pat. No. 6,393,316, which is hereby incorporated herein by reference.

In accordance with another embodiment, rhythm discrimination may be based on a morphological analysis of the area under the peaks of detected cardiac waveforms and known template waveforms (e.g., NSR, VT, SVT template waveforms). For example, a template based on morphology of a normal sinus rhythm may be collected. A sensed cardiac signal is compared against the template to determine how closely the sensed and template signals correspond based on morphology. The comparison may be done based on peak information in the template and the sensed signal.

A score may be generated to indicate the degree of similarity between the template and the sensed signal. Peak information may be extracted in the following manner. A group of three consecutive peaks having a largest cumulative peak amplitude is located in the template and in the sensed signal. The polarity, position and area of each peak within the group is then determined. The area of each peak is normalized. The polarities, positions and normalized areas represent the peak information that is used for comparison. Details of suitable area-based morphological analysis techniques that may be implemented by an EDA of the present invention are disclosed in U.S. Pat. No. 5,779,645, which is hereby incorporated herein by reference.

With further reference to FIG. 5, if the discrimination algorithm implemented on the APM server determines, to a specified degree of certainty (certainty X and Y shown in blocks 424 and 426) that the event was incorrectly classified by the implantable cardiac device, then the classification of the event as determined by the APM server-based discrimination algorithm may be used to modify 440 the discrimination algorithm (e.g., one or more parameters and/or templates) implemented by the implantable cardiac device. For example, if the APM-server's EDA classifies a given rhythm as SVT rather than VT (as was classified by the implantable cardiac device), then the APM server would update the SVT template 440 in the implantable device to reflect the new classification and notify the physician that an update has been made to the SVT template.

Alternatively, the APM server could notify the physician 430 that the event was incorrectly classified by the implanted device and ask the physician whether the SVT template should be updated accordingly. If and when the physician responds affirmatively, the APM server-based algorithm then automatically updates the SVT template 434, 440. If the APM server-based algorithm cannot classify the event, then the physician would be notified and physician intervention would be required.

The methodology depicted in FIG. 5 provides for external computational resources that can be leveraged to automatically classify a patient's tachyarrhythmia events off-line using an algorithm(s) that is/are too computationally intensive to be run on an implantable device platform. Automatic classification can then be used to update morphological templates in order to improve the performance of morphology-based VT/SVT discrimination algorithms. In addition, an external discrimination algorithm implemented by an APM sever or other external processor can be used to validate an implantable device's classification of a tachyarrhythmia and notify the physician if discrepancies exist between the device classification and a remote system classification. Another useful function involves notifying the physician of the presence of anomalous rhythms which cannot be automatically classified by either the device or a remote system.

Figure 6:
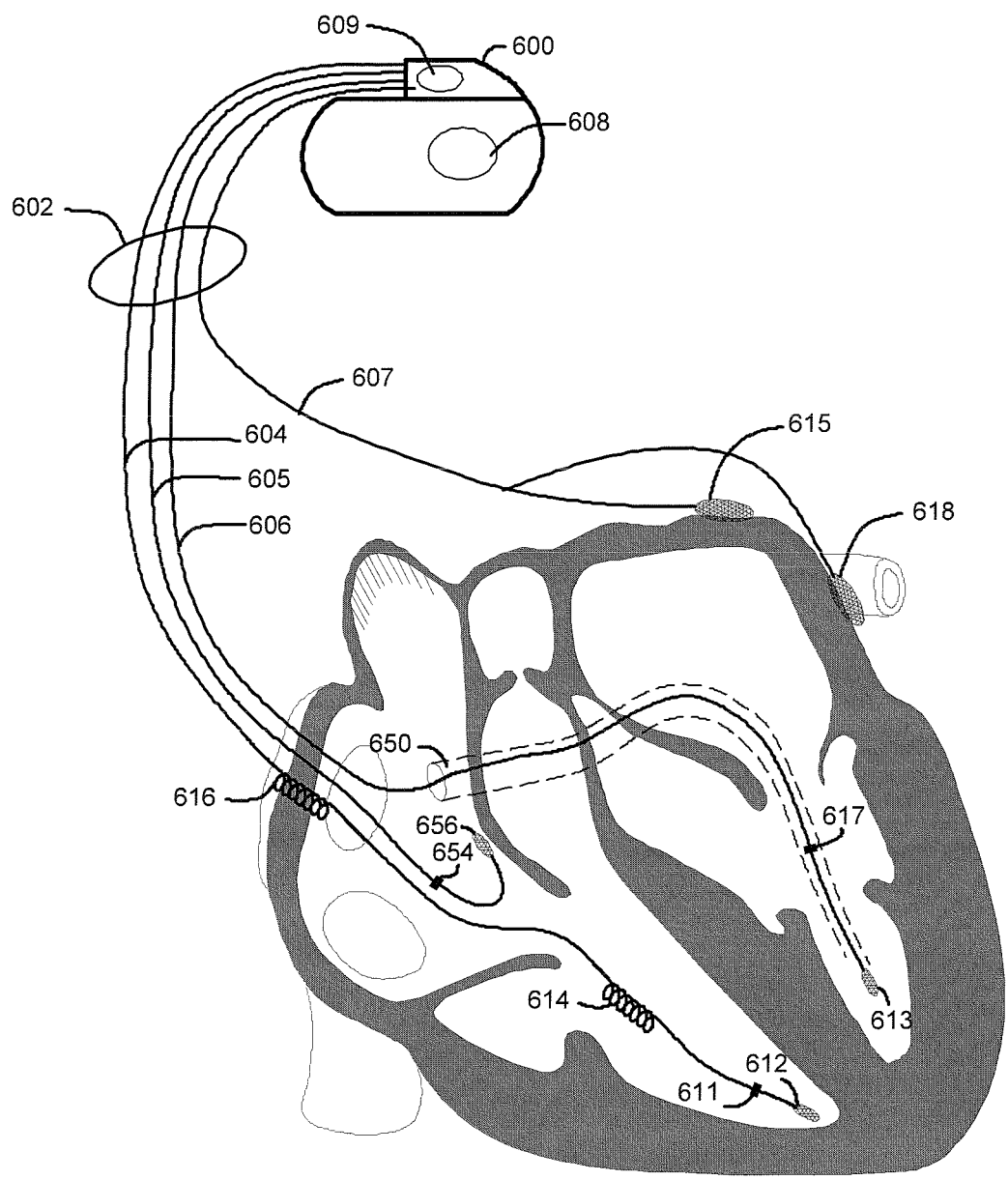
FIG. 6 is a diagram of an implantable cardiac device with leads implanted within a patient's heart, the implantable cardiac device implementing discrimination algorithms in accordance with embodiments of the present invention.

Referring now to FIG. 6, there is shown a cardiac rhythm management (CRM) system that may be used to implement rhythm discrimination and/or validation in accordance with the approaches of the present invention. The CRM system in FIG. 6 includes a pacemaker/defibrillator 600 enclosed within a housing and coupled to a lead system 602. The housing and/or header of the pacemaker/defibrillator 600 may incorporate one or more can or indifferent electrodes 608, 609 used to provide electrical stimulation energy to the heart and/or to sense cardiac electrical activity. The pacemaker/defibrillator 600 may utilize all or a portion of the device housing as a can electrode 608. The pacemaker/defibrillator 600 may include an indifferent electrode 609 positioned, for example, on the header or the housing of the pacemaker/defibrillator 600. If the pacemaker/defibrillator 600 includes both a can electrode 608 and an indifferent electrode 609, the electrodes 608, 609 typically are electrically isolated from each other.

The lead system 602 is used to detect cardiac electrical signals produced by the heart and to provide electrical energy to the heart under certain predetermined conditions to treat cardiac arrhythmias. The lead system 602 may include one or more electrodes used for pacing, sensing, and/or defibrillation. In the embodiment shown in FIG. 6, the lead system 602 includes an intracardiac right ventricular (RV) lead system 604, an intracardiac right atrial (RA) lead system 605, and an intracardiac left ventricular (LV) lead system 606. An extracardiac left atrial (LA) lead system 607 is employed.

The CRM system illustrated in FIG. 6 is configured for biventricular or biatrial pacing. The lead system 602 of FIG. 6 illustrates one embodiment that may be used in connection with the rhythm discrimination and/or validation processes described herein. Other leads and/or electrodes may additionally or alternatively be used. For example, the CRM system may pace multiple sites in one cardiac chamber via multiple electrodes within the chamber. This type of multisite pacing may be employed in one or more of the right atrium, left atrium, right ventricle or left ventricle. Multisite pacing in a chamber may be used for example, to increase the power and or synchrony of cardiac contractions of the paced chamber.

The lead system 602 may include intracardiac leads 604, 605, 606 implanted in a human body with portions of the intracardiac leads 604, 605, 606 inserted into a heart. The intracardiac leads 604, 605, 606 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 602 may include one or more extracardiac leads 607 having electrodes 615, 618, e.g., epicardial electrodes, positioned at locations outside the heart for sensing and pacing one or more heart chambers. In some configurations, the epicardial electrodes may be placed on or about the outside of the heart and/or embedded in the myocardium from locations outside the heart. The right ventricular lead system 604 illustrated in FIG. 6 includes an SVC-coil 616, an RV-coil 614, an RV-ring electrode 611, and an RV-tip electrode 612. The right ventricular lead system 604 extends through the right atrium and into the right ventricle.

In particular, the RV-tip electrode 612, RV-ring electrode 611, and RV-coil electrode 614 are positioned at appropriate locations within the right ventricle for sensing and delivering electrical stimulation pulses to the heart. The SVC-coil 616 is positioned at an appropriate location within the right atrium chamber of the heart or a major vein leading to the right atrial chamber.

In one configuration, the RV-tip electrode 612 referenced to the can electrode 608 may be used to implement unipolar pacing and/or sensing in the right ventricle. Bipolar pacing and/or sensing in the right ventricle may be implemented using the RV-tip 612 and RV-ring 611 electrodes. In yet another configuration, the RV-ring 611 electrode may optionally be omitted, and bipolar pacing and/or sensing may be accomplished using the RV-tip electrode 612 and the RV-coil 614, for example. The right ventricular lead system 604 may be configured as an integrated bipolar pace/shock lead. The RV-coil 614 and the SVC-coil 616 are defibrillation electrodes.

The left ventricular lead 606 includes an LV distal electrode 613 and an LV proximal electrode 617 located at appropriate locations in or about the left ventricle for pacing and/or sensing the left ventricle. The left ventricular lead 606 may be guided into the right atrium of the heart via the superior vena cava. From the right atrium, the left ventricular lead 606 may be deployed into the coronary sinus ostium, the opening of the coronary sinus 650. The lead 606 may be guided through the coronary sinus 650 to a coronary vein of the left ventricle. This vein is used as an access pathway for leads to reach the surfaces of the left ventricle which are not directly accessible from the right side of the heart. Lead placement for the left ventricular lead 606 may be achieved via subclavian vein access and a preformed guiding catheter for insertion of the LV electrodes 613, 617 adjacent to the left ventricle.

Unipolar pacing and/or sensing in the left ventricle may be implemented, for example, using the LV distal electrode referenced to the can electrode 608. The LV distal electrode 613 and the LV proximal electrode 617 may be used together as bipolar sense and/or pace electrodes for the left ventricle. The lead system 602 in conjunction with the pacemaker/defibrillator 600 may provide bradycardia pacing therapy to maintain a hemodynamically sufficient heart rate. The left ventricular lead 606 and the right ventricular lead 604 and/or the right atrial lead and the left atrial lead may be used to provide cardiac resynchronization therapy such that the ventricles and/or atria of the heart are paced substantially simultaneously or in phased sequence separated by an interventricular or interatrial pacing delay, to provide enhanced cardiac pumping efficiency for patients suffering from congestive heart failure.

The right atrial lead 605 includes a RA-tip electrode 656 and an RA-ring electrode 654 positioned at appropriate locations in the right atrium for sensing and pacing the right atrium. In one configuration, the RA-tip 656 referenced to the can electrode 608, for example, may be used to provide unipolar pacing and/or sensing in the right atrium. In another configuration, the RA-tip electrode 656 and the RA-ring electrode 654 may be used to effect bipolar pacing and/or sensing.

Figure 7:
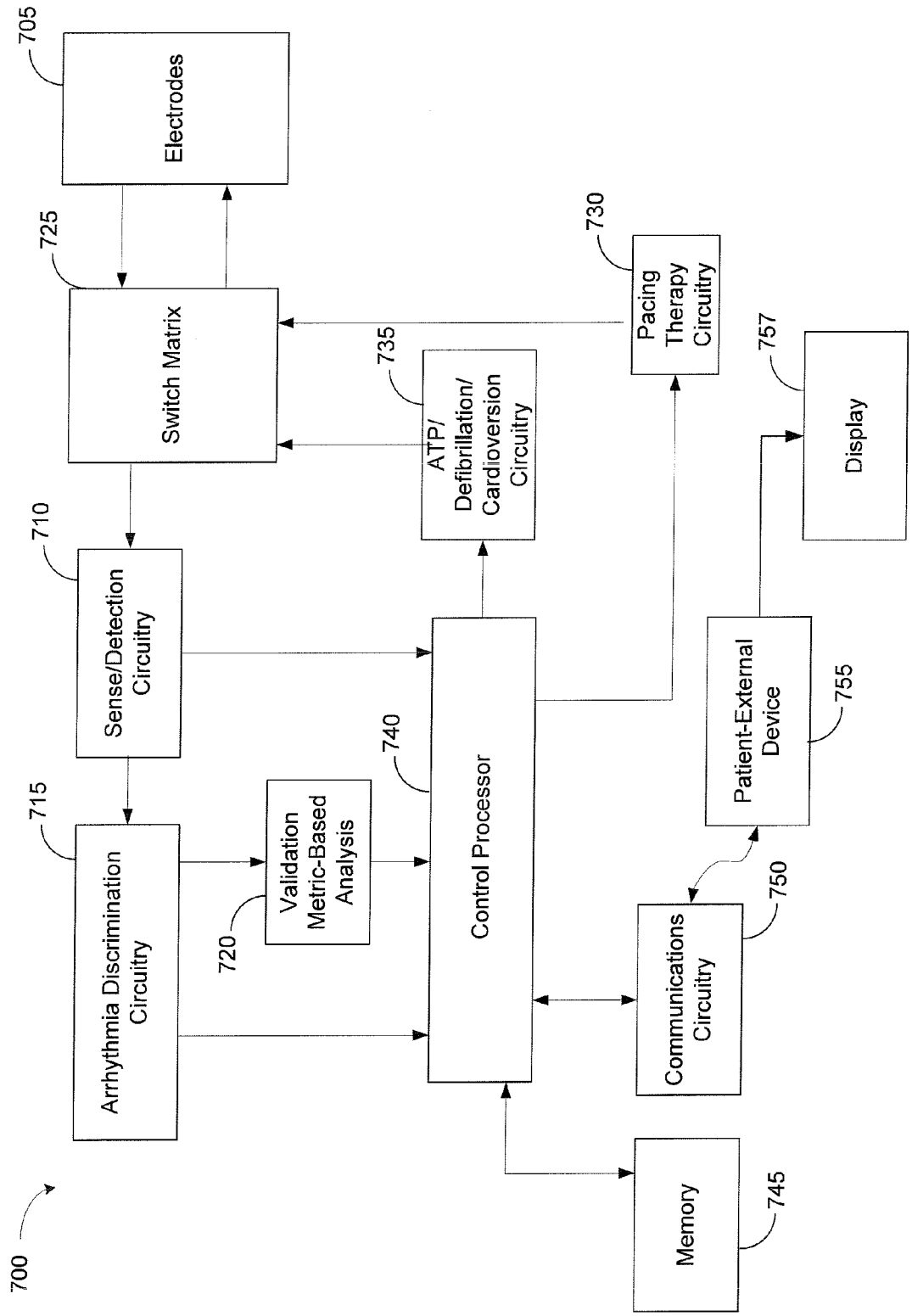
FIG. 7 is a block diagram of various components of an implantable cardiac device that implements discrimination algorithms in accordance with embodiments of the present invention.

Referring now to FIG. 7, there is shown a block diagram of an embodiment of an implantable CRM system 700 suitable for implementing rhythm discrimination and/or validation approaches of the present invention. FIG. 7 shows a CRM system 700 divided into functional blocks. It is understood by those skilled in the art that there exist many possible configurations in which these functional blocks can be arranged. The example depicted in FIG. 7 is one possible functional arrangement. Other arrangements are also possible. For example, more, fewer or different functional blocks may be used to describe a cardiac system suitable for implementing rhythm discrimination and/or validation processes of the present invention. In addition, although the CRM system 700 depicted in FIG. 7 contemplates the use of a programmable microprocessor-based logic circuit, other circuit implementations may be utilized.

The CRM system 700 includes a control processor 740 capable of controlling the delivery of pacing pulses or defibrillation shocks to the right ventricle, left ventricle, right atrium and/or left atrium. The pacing therapy circuitry 730 is configured to generate pacing pulses for treating bradyarrhythmia, for example, or for synchronizing the contractions of contralateral heart chambers using biatrial and/or biventricular pacing.

The CRM system 700 includes arrhythmia discrimination circuitry 715 configured to classify cardiac rhythms, such as by use of rate-based and/or morphological-based algorithms operating on detected cardiac signals. The arrhythmia discrimination circuitry 715 typically operates to detect atrial and/or ventricular tachyarrhythmia or fibrillation using a multiplicity of discrimination algorithms. Rhythm discrimination circuitry 715 or the control processor 740 may be configured to implement a validation metric-based discrimination analysis 720 as described above. Under control of the control processor 740, the pacing/cardioversion/defibrillation circuitry 735 is capable of generating high energy shocks to terminate the tachyarrhythmia episodes (e.g., antitachycardia pacing (ATP), cardioversion, and defibrillation therapies), as determined by the arrhythmia discriminator circuitry 715 and verified by the validation metric-based analysis.

The pacing pulses and/or defibrillation shocks are delivered via multiple cardiac electrodes 705 electrically coupled to a heart and disposed at multiple locations within, on, or about the heart. One or more electrodes 705 may be disposed in, on, or about each heart chamber or at multiple sites of one heart chamber. The electrodes 705 are coupled to switch matrix 725 circuitry that is used to selectively couple the electrodes 705 to the sense circuitry 710 and the therapy circuitry 730, 735.

The CRM system 700 is typically powered by an electrochemical battery (not shown). A memory 745 stores data (electrograms from multiple channels, timing data, etc.) and program commands used to implement the rhythm discrimination and/or validation approaches described herein along with other features. Data and program commands may be transferred between the CRM system 700 and a patient-external device 755 via telemetry-based communications circuitry 750.

The patient-external device 755 may be implemented as a programmer, an APM system or other external computational resource. A display 757 of a user interface of the patient-external device 755 is typically provided to facilitate user interaction with the patient-external device 755 and implantable cardiac device. Data transferred from the implantable cardiac device to the patient-external device 755 may be organized for presentation in an arrhythmia logbook format as discussed previously. A clinician or physician may review electrograms and related data for troubleshooting and adjusting device programming. A physician may review electrograms on the display 757 and generate SVT templates via a user interface of the patient-external device 755 in a manner described hereinabove.

The components, functionality, and structural configurations depicted herein are intended to provide an understanding of various features and combination of features that may be incorporated in an implantable cardiac device, such as a pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A system, comprising:
    an implantable cardiac device (ICD), comprising:
        sensing circuitry configured to sense cardiac electrical activity;
        energy delivery circuitry configured to deliver cardiac electrical therapy to treat cardiac tachyarrhythmias;
        a local processor coupled to the sensing circuitry and the energy delivery circuitry;
        a local memory coupled to the local processor and configured to store a plurality of cardiac tachyarrhythmia discrimination algorithms and LCD data produced by the local processor, the ICD data comprising data associated with a plurality of cardiac tacharrhythmic episodes classified by the ICD based on the plurality of tachyarrhythmia discrimination algorithms; and
        communications circuitry coupled to the local processor; and
    an external device, comprising:
        a communications interface configured to receive the LCD data;
        an external memory configured to store the LCD data and an external discrimination algorithm (EDA) different from the cardiac tachyarrhythmia discrimination algorithms stored in the ICD, the EDA comprising one or more cardiac tachyarrhythmia discrimination algorithms requiring computational resources exceeding those offered by the ICD; and
        an external processor coupled to the communications interface and the external memory, the external processor configured to apply the EDA to the ICD data stored in the external memory to automatically classify the plurality of cardiac tacharrhythmic episodes classified by the ICD without requiring user intervention, the external processor configured to generate a validation metric based on a comparison between the ICD and external device classifications of each of the plurality of cardiac tacharrhythmic episodes, the validation metric indicative of a level of confidence of the ICD properly classifying the plurality of cardiac tacharrhythmic episodes.

2. The system of claim 1, wherein the external processor is configured to determine a discrepancy or agreement between the ICD and external device episode classifications of each of the cardiac tacharrhythmic episodes.

3. The system of claim 1, wherein the external processor is configured to determine a discrepancy or agreement between the ICD and external device episode classifications of each of the cardiac tacharrhythmic episodes relative to a predetermined certainty threshold.

4. The system of claim 1 wherein the external processor is configured to determine to a first specified degree of certainty whether each of the cardiac tacharrhythmic episodes was correctly classified by the ICD.

5. The system of claim 1, wherein the external processor is configured to determine to a second specified degree of certainty whether each of the cardiac tacharrhythmic episodes was incorrectly classified by the ICD.

6. The system of claim 1, wherein the external processor is configured to:
determine to a first specified degree of certainty whether each of the cardiac tacharrhythmic episodes was correctly classified by the ICD; and
determine to a second specified degree of certainty whether each of the cardiac tacharrhythmic episodes was incorrectly classified by the ICD;
wherein the first and second specified degrees of certainty are adjustable 7. The system of claim 1, wherein the external processor is configured to:
determine to a second specified degree of certainty whether each of the cardiac tacharrhythmic episodes was incorrectly classified by the ICD; and
flag the cardiac tacharrhythmic episodes that were incorrectly classified by the ICD and failed to exceed the second specified degree of certainty.

8. The system of claim 1, wherein the external processor is configured to:
determine to a second specified degree of certainty whether each of the cardiac tacharrhythmic episodes was incorrectly classified by the ICD;
flag the cardiac tacharrhythmic episodes that were incorrectly classified by the ICD and failed to exceed the second specified degree of certainty;
receive a physician authorized update for one or more of the ICD cardiac tacharrhythmia discrimination algorithms associated with the flagged cardiac tacharrhythmic episodes confirmed as incorrectly classified by the ICD; and
transmit the update to the ICD for incorporation in the local memory of the ICD.

9. The system of claim 1, wherein the external processor is configured to:
determine to a second specified degree of certainty whether each of the cardiac tacharrhythmic episodes was incorrectly classified by the ICD;
algorithmically generate an update for one or more of the ICD cardiac tacharrhythmia discrimination algorithms associated with the cardiac tacharrhythmic episodes incorrectly classified by the ICD and exceeding the second specified degree of certainty; and
transmit the update to the ICD for incorporation in the local memory of the ICD.

10. A system, comprising:
an implantable cardiac device (ICD), comprising:
sensing circuitry configured to sense cardiac electrical activity;
energy delivery circuitry configured to deliver cardiac electrical therapy to treat cardiac tachyarrhythmias;
a local processor coupled to the sensing circuitry and the energy delivery circuitry;
a local memory coupled to the local processor and configured to store one or more cardiac signal templates, a plurality of cardiac tachyarrhythmia discrimination algorithms, and ICD data produced by the local processor, the ICD data comprising data associated with a plurality of cardiac tacharrhythmic episodes classified by the ICD using the plurality of tachyarrhythmia discrimination algorithms and the one or more cardiac signal templates; and
communications circuitry coupled to the local processor; and
an external device, comprising:
a communications interface configured to receive the ICD data;
an external memory configured to store the ICD data, an external discrimination algorithm (EDA) different from the cardiac tachyarrhythmia discrimination algorithms stored in the ICD, and one or more supraventricular tachycardia (SVT) templates, the EDA comprising one or more cardiac tachyarrhythmia discrimination algorithms requiring computational resources exceeding those offered by the ICD; and
an external processor coupled to the communications interface and the external memory, the external processor configured to apply the EDA to the ICD data stored in the external memory to automatically classify the plurality of cardiac tacharrhythmic episodes classified by the ICD relative to the one or more SVT templates without requiring user intervention, the external processor configured to generate a validation metric based on a misclassification of one or more of the plurality of cardiac tacharrhythmic episodes by the ICD, the validation metric indicative of a level of confidence of the ICD properly classifying the plurality of cardiac tacharrhythmic episodes.

11. The system of claim 10, wherein the external processor is configured to generate a modification to one or more of the ICD cardiac tachyarrhythmia discrimination algorithms or cardiac signal templates based on the one or more cardiac tacharrhythmic episodes misclassified by the ICD, and transmit the modification to the ICD for incorporation in the local memory.

12. The system of claim 10, wherein the external processor is configured to generate an updated SVT template based on the one or more cardiac tacharrhythmic episodes misclassified by the ICD, and transmit the updated SVT template to the ICD for incorporation in the local memory.

13. The system of claim 10, wherein the external processor is configured to generate an updated SVT template based on a cardiac tachyarrhythmic episode misclassified as a ventricular tachyarrhythmic episode by the ICD, and transmit the updated SVT template to the ICD for incorporation in the local memory.

14. The system of claim 13, wherein the external processor is configured to generate a physician alert in response to transmission of the updated SVT template to the ICD.

15. The system of claim 10, wherein the external processor is configured to automatically generate an SVT template for tachyarrhythmic episodes for which the cardiac tachyarrhythmia episode classifications respectively made by the EDA and the ICD are in disagreement and a comparison of the respective classifications exceeds a specified degree of certainty.

16. The system of claim 10, wherein the external processor is configured to:
compare the cardiac tachyarrhythmia episode classifications respectively made by the EDA and the ICD and determine if disagreement between the respective classifications exceeds a specified degree of certainty;
flag tachyarrhythmic episodes for clinician review in response to disagreement between the respective classifications failing to exceed the specified degree of certainty;
generate an SVT template for selected ones of the flagged arrhythmic episodes in response to a clinician input; and
transmit the generated SVT template or templates to the ICD for incorporation in the local memory.

17. The system of claim 10, wherein the output generated by the external processor comprises a physician alert or notification.

18. A method, comprising:
storing a plurality of cardiac tachyarrhythmia discrimination algorithms in an implantable cardiac device (ICD);
classifying a plurality of cardiac tacharrhythmic episodes by the ICD using the plurality of tachyarrhythmia discrimination algorithms;
producing ICD data associated with the plurality of cardiac tacharrhythmic episodes including ICD classification data;
receiving the ICD data by an external system;
applying an external discrimination algorithm (EDA) to the received ICD data by the external system, the EDA different from the cardiac tachyarrhythmia discrimination algorithms stored in the ICD, the EDA comprising one or more cardiac tachyarrhythmia discrimination algorithms requiring computational resources exceeding those offered by the ICD;
automatically classifying the plurality of cardiac tacharrhythmic episodes classified by the ICD using the EDA without requiring user intervention; and
generating, by the external system, a validation metric based on a comparison between the ICD and external device classifications of each of the plurality of cardiac tacharrhythmic episodes, the validation metric indicative of level of confidence of the ICD properly classifying the plurality of cardiac tacharrhythmic episodes.

19. The method of claim 18, wherein generating the output comprises:
generating, by the external system, a modification to one or more of the ICD cardiac tachyarrhythmia discrimination algorithms based on one or more cardiac tacharrhythtnic episodes misclassified by the ICD; and
transmitting the modification from the external system to the ICD for incorporation therein.

20. The method of claim 18, comprising:
determining to a first specified degree of certainty whether each of the cardiac tacharrhythmic episodes was correctly classified by the ICD;
determining to a second specified degree of certainty whether each of the cardiac tacharrhythmic episodes was incorrectly classified by the ICD; and
adjusting one or both of the first and second specified degrees of certainty;
wherein each of the respective determining and adjusting processes is implemented at least in part by the external system.

* * * * *